United States Patent [19]

Berg

[11] Patent Number: 5,458,741

[45] Date of Patent: Oct. 17, 1995

[54] SEPARATION OF BENZENE FROM CLOSE BOILING HYDROCARBONS BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,047

[22] Filed: Jan. 14, 1994

[51] Int. Cl.[6] .................. B01D 3/40; C07C 7/08
[52] U.S. Cl. .................. 203/57; 203/58; 203/60; 203/62; 203/63; 203/65; 585/803; 585/804; 585/808; 585/857; 585/860; 585/862; 585/864; 585/865; 585/866
[58] Field of Search ............... 203/57, 60, 62, 203/58, 63, 65; 585/860, 862, 803, 864, 866, 865, 804, 808, 856, 857

[56] References Cited

U.S. PATENT DOCUMENTS

| | | | |
|---|---|---|---|
| 2,834,822 | 5/1958 | Worthington et al. | 585/807 |
| 2,842,484 | 7/1958 | Fleck | 203/51 |
| 3,227,632 | 1/1966 | Schmalenbach et al. | 203/58 |
| 3,884,769 | 5/1975 | Mikitenko et al. | 203/53 |
| 4,053,369 | 10/1977 | Cines | 203/58 |
| 4,514,262 | 4/1985 | Berg | 203/51 |
| 5,399,244 | 3/1995 | Gentry et al. | 203/57 |

FOREIGN PATENT DOCUMENTS

| | | | |
|---|---|---|---|
| 767693 | 10/1971 | Belgium | 585/808 |
| 52-05733 | 1/1977 | Japan | 203/58 |
| 1139537 | 6/1989 | Japan | 585/866 |

*Primary Examiner*—Wilbur Bascomb, Jr.

[57] ABSTRACT

Benzene is difficult to separate from cyclohexane or cyclohexene by conventional distillation or rectification because of the close proximity of their boiling points. Benzene can be readily separated from cyclohexane or cyclohexene by using extractive distillation. Effective agents are: for benzene from cyclohexane, methyl acetoacetate; for benzene from cyclohexene, ethyl acetoacetate.

2 Claims, No Drawings

SEPARATION OF BENZENE FROM CLOSE BOILING HYDROCARBONS BY EXTRACTIVE DISTILLATION

FIELD OF THE INVENTION

This invention relates to a method for separating benzene from close boiling hydrocarbons using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Benzene boils at 80.1° C. The hydrocarbons boiling closest to benzene are cyclohexane, B.P. 80.8° C. and cyclohexene, B.P. 83.2° C. The relative volatility of benzene to cyclohexane is 1.02, of benzene to cyclohexene is 1.1.

TABLE 1

Theoretical and Actual Plates Required vs. Relative Volatility for Benzene - Cyclohexane - Cyclohexene Separation

| Relative Volatility | Theoretical Plates Required At Total Reflux, 99% Purity | Actual Plates Required, 75% Eff. |
|---|---|---|
| 1.02 | 470 | 630 |
| 1.1 | 96 | 128 |
| 1.2 | 50 | 67 |
| 1.5 | 23 | 31 |
| 2.0 | 14 | 19 |
| 2.4 | 11 | 15 |
| 2.6 | 10 | 14 |

Table 1 shows that benzene cannot be separated practically from cyclohexane by conventional rectification. To separate benzene from cyclohexene in 99% purity requires 128 actual plates. For an agent giving a relative volatility of 2.0, nineteen actual plates are required, with 2.6 it is only fourteen plates.

OBJECTIVE OF THE INVENTION

The object of this invention is to provide a process or method of extractive distillation that will enhance the relative volatility of benzene to cyclohexane and cyclohexene in their separation in a rectification column. It is a further object of this invention to identify certain organic compounds that are stable, are effective extractive distillation agents and can be recycled to the extractive distillation column with little decomposition.

SUMMARY OF THE INVENTION

The objects of this invention are provided by a process for the separation of benzene from cyclohexane and cyclohexene which entails the use of certain organic compounds when employed as the agent in extractive distillation.

DETAILED DESCRIPTION OF THE INVENTION

I have discovered that certain organic compounds will effectively increase the relative volatility between benzene and cyclohexane and between benzene and cyclohexene when employed as the agent in extractive distillation. Table 2 summarizes the data obtained with these agents.

The compounds which are effective extractive distillation agents are dimethylsulfoxide, dimethoxymethane, propyl formate, methyl valerate, 1-methoxy-2-propanol, ethyl caproate, methyl caproate, ethyl isobutyrate, hexyl acetate, ethyl acetoacetate, methyl acetoacetate, ethyl acetate, n-propyl acetate, propyl caproate, isopropyl acetate, isobutyl acetate, isoamyl formate, 2-furaldehyde, phenol, o-cresol, m-p-cresol, 3,5-dimethyl phenol, o-tert. butyl phenol, p-cresol, o-sec. butyl phenol, 2,4-dimethyl phenol, 2-isopropyl phenol, 3-ethyl phenol, 4-nitrophenol and butyl formate for separating benzene from cyclohexane. Those that are effective for separating benzene from cyclohexene are isoamyl formate, dimethylformamide, dimethylsulfoxide, ethyl acetoacetate, methyl acetoacetate, ethyl acetate, phenol, o-sec. butyl phenol, 4-nitro phenol, 2-furaldehyde and isobutyl butyrate.

TABLE 2

Effective Extractive Distillation Agents For Separating Benzene From Cyclohexane And/Or Cyclohexene

| Compounds | Relative Volatility Cyclohexane - Benzene | Relative Volatility Cyclohexene - Benzene |
|---|---|---|
| None | 1.02 | 1.11 |
| Dimethylsulfoxide | 1.75 | 1.85 |
| Dimethoxymethane | 1.65 | |
| Propyl formate | 2.7 | |
| Methyl valarate | 1.45 | |
| 1-methoxy-2-propanol | 1.65 | |
| Ethyl caproate | 1.4 | |
| Methyl caproate | 1.4 | |
| Isoamyl formate | 1.45 | 1.4 |
| Ethyl isobutyrate | 1.4 | |
| Hexyl acetate | 1.35 | |
| Ethyl acetoacetate | 1.7 | 1.85 |
| Methyl acetoacetate | 2.0 | 1.35 |
| Ethyl acetate | 1.6 | 1.25 |
| n-Propyl acetate | 1.55 | |
| Propyl caproate | 1.35 | |
| Isopropyl acetate | 1.5 | |
| Isobutyl acetate | 1.4 | |
| Dimethyl formamide | | 1.6 |
| 2-Furaldehyde | 2.1 | 1.45 |
| Phenol | 1.8 | 1.2 |
| o-Cresol | 1.65 | |
| m-p-Cresol | 1.6 | |
| p-Cresol | 1.6 | |
| 3,5-Dimethyl phenol | 1.55 | |
| o-tert. Butyl phenol | 1.45 | |
| o-sec. Butyl phenol | 1.45 | 1.8 |

TABLE 2-continued

Effective Extractive Distillation Agents For Separating Benzene From Cyclohexane And/Or Cyclohexene

| Compounds | Relative Volatility Cyclohexane - Benzene | Relative Volatility Cyclohexene - Benzene |
|---|---|---|
| 2,4-Dimethyl phenol | 1.55 | |
| 2-Isopropyl phenol | 1.55 | |
| 3-Ethyl phenol | 1.6 | |
| 4-Nitro phenol | 1.6 | 1.2 |
| Butyl formate | 1.6 | |
| Isobutyl butyrate | | 1.55 |

THE USEFULNESS OF THE INVENTION

The usefulness or utility of this invention can be demonstrated by referring to the data presented in Tables 1 and 2. All of the successful agents show that benzene can be separated from cyclohexane and/or cyclohexene by means of extractive distillation in a rectification column and that the ease of separation as measured by relative volatility is considerable.

WORKING EXAMPLES

Example 1

Eighty grams of benzene, 20 grams of cyclohexane and 50 grams of methyl acetoacetate were charged to a vapor-liquid equilibrium still and refluxed for seven hours. Analysis indicated a vapor composition of 27% cyclohexane, 73% benzene, a liquid composition of 15.6% cyclohexane, 84.4% benzene. This is a relative volatility of 2.0.

Example 2

Eighty grams of benzene, 20 grams of cyclohexene and 50 grams of ethyl acetoacetate were charged to a vapor-liquid equilibrium still and refluxed for four hours. Analysis indicated a vapor composition of 28.4% cyclohexene, 71.6% benzene; a liquid composition of 21.1% cyclohexene, 78.9% benzene. This is a relative volatility of 1.48.

I claim:

1. A method for recovering benzene from a mixture of cyclohexane and benzene which comprises distilling a mixture of cyclohexane and benzene in a rectification column in the presence of about one part by weight of an extractive agent per part of cyclohexane - benzene mixture, recovering the cyclohexane as overhead product and obtaining the benzene and the extractive agent from the stillpot, wherein said extractive agent consists of one material selected from the group consisting of dimethoxymethane, propyl formate, methyl valerate, 1-methoxy-2-propanol, ethyl caproate, methyl caproate, ethyl acetate, ethyl isobutyrate, hexyl acetate, methyl acetoacetate, n-propylcaproate, isopropyl acetate, isobutyl acetate, isoamyl formate, 4-nitro phenol, butyl formate and n-propyl acetate.

2. A method for recovering benzene from a mixture of cyclohexene and benzene which comprises distilling a mixture of cyclohexene and benzene in a rectification column in the presence of about one part by weight of an extractive agent per part of cyclohexene - benzene mixture, recovering the cyclohexene as overhead product and obtaining the benzene and the extractive agent from the stillpot, wherein said extractive agent consists of one material selected from the group consisting of isoamyl formate, methyl acetoacetate, ethyl acetate, 4-nitrophenol and isobutyl butyrate.

* * * * *